US011291714B2

(12) United States Patent
Kim et al.

(10) Patent No.: US 11,291,714 B2
(45) Date of Patent: Apr. 5, 2022

(54) RECOMBINANT ANTIGEN DERIVED FROM ZIKA VIRUS E PROTEIN AND USE THEREOF

(71) Applicant: Korea Center For Disease Control And Prevention, Chungcheongbuk-do (KR)

(72) Inventors: You-Jin Kim, Chungcheongbuk-do (KR); Hyun Ju In, Chungcheongbuk-do (KR); HeeJi Lim, Chungcheongbuk-do (KR); Sun-Dong Jang, Chungcheongbuk-do (KR); Jung-Sik Yoo, Chungcheongbuk-do (KR); Gyung Tae Chung, Chungcheongbuk-do (KR)

(73) Assignee: Korea Center for Disease Control and Prevention, Cheongju-si (KR)

( * ) Notice: Subject to any disclaimer, the term of this patent is extended or adjusted under 35 U.S.C. 154(b) by 12 days.

(21) Appl. No.: 16/708,797

(22) Filed: Dec. 10, 2019

(65) Prior Publication Data

US 2020/0230227 A1 Jul. 23, 2020

(30) Foreign Application Priority Data

Dec. 12, 2018 (KR) ........................ 10-2018-0160420

(51) Int. Cl.

| | |
|---|---|
| ***A61K 39/12*** | (2006.01) |
| ***C07K 14/005*** | (2006.01) |
| ***C12N 7/00*** | (2006.01) |
| ***C07K 16/10*** | (2006.01) |
| ***C12N 15/70*** | (2006.01) |
| ***C12N 1/20*** | (2006.01) |
| *A61K 39/00* | (2006.01) |
| *C12R 1/19* | (2006.01) |

(52) U.S. Cl.

CPC ............ *A61K 39/12* (2013.01); *C07K 14/005* (2013.01); *C07K 16/1081* (2013.01); *C12N 1/205* (2021.05); *C12N 7/00* (2013.01); *C12N 15/70* (2013.01); *A61K 2039/575* (2013.01); *C07K 2317/76* (2013.01); *C12N 2770/24122* (2013.01); *C12N 2770/24134* (2013.01); *C12R 2001/19* (2021.05)

(58) Field of Classification Search

None

See application file for complete search history.

(56) References Cited

U.S. PATENT DOCUMENTS

| | | | | |
|---|---|---|---|---|
| 2017/0252425 | A1 | 9/2017 | Akahata et al. | |
| 2018/0340181 | A1* | 11/2018 | Chen | A61K 39/12 |

FOREIGN PATENT DOCUMENTS

| | | | | |
|---|---|---|---|---|
| EP | 3184118 | A1 | 6/2017 | |
| EP | 3412307 | A1 * | 12/2018 | A61K 39/12 |
| KR | 20180036987 | A | 4/2018 | |
| WO | 2018020271 | A1 | 2/2018 | |
| WO | 2018115509 | A2 | 6/2018 | |

OTHER PUBLICATIONS

Pattnaik et al., Vaccines, 2020, 8, 266, 19 pages. (Year: 2020).*
Ayllón et al., Research Letters, Aug. 2017, 23(8):1411-1412. (Year: 2017).*
Gen Bank accession No. KY354184 (2017) (Year: 2017).*
Safdari et al., Biotechnology and Genetic Engineering Reviews, 2013, 29(2):175-186. (Year: 2013).*
Muthumani et al., Npj Vaccines, 2006, 1, 16021, 11 pages. (Year: 2006).*
Grunwald et al., Clin Exp Vaccine Res, 2015, 4:1-10. (Year: 2015).*
Tai, Wanbo, et al., “Critical neutralizing fragment of Zika virus EDIII elicits cross-neutralization and protection against divergent Zika viruses”, Emerging Microbes & Infections (2018)7:7, 13 pages.

* cited by examiner

*Primary Examiner* — Stacy B Chen
(74) *Attorney, Agent, or Firm* — Servilla Whitney LLC

(57) ABSTRACT

The present invention relates to a recombinant antigen derived from Zika virus E protein and use thereof. Specifically, the present invention provides a polynucleotide encoding Zika virus E protein domain III alone or repeatedly three times, a recombinant plasmid vector comprising the polynucleotide, and a DNA vaccine composition that may induce an immune response to Zika virus by expressing a Zika virus antigen protein effectively. In addition, the present invention provides a neutralizing antibody against Zika virus obtained using the polynucleotide and a method for preparing the neutralizing antibody.

17 Claims, 6 Drawing Sheets

Specification includes a Sequence Listing.

SEQUENCE LISTING

```
<160> NUMBER OF SEQ ID NOS: 14

<210> SEQ ID NO 1
<211> LENGTH: 969
```

<212> TYPE: DNA
<213> ORGANISM: Artificial Sequence
<220> FEATURE:
<223> OTHER INFORMATION: Codon opti ED3

<400> SEQUENCE: 1
ggagtgagct atagtctgtg tacagccgct tttacattca ctaagatccc agccgaaacc 60
cttcacggaa cagtgacagt ggaagtgcag tacgctggaa ctgacggacc atgtaaggtg 120
ccagctcaga tggccgtgga tatgcaaaca ctgacacccg tgggaagact gatcacagct 180
aatccagtga ttactgaatc tacagagaat agcaaaatga tgctggaact tgacccccca 240
tttggagact catatattgt gatcggcgtg ggcgagaaga agatcaccca ccactggcat 300
agatccggca gcacgggggg cggcggaggc gtgagctaca gcctgtgcac cgccgccttc 360
acctttacca agatcccagc cgagacgctg cacggcacag tgaccgtgga ggtgcagtac 420
gccggaaccg acggaccatg caaggtgcca gcccagatgg ctgtggacat gcagaccctg 480
acccccgtgg gcagactgat caccgccaac ccagtgatca cagagtctac cgagaacagc 540
aagatgatgc tggaactgga cccacccttc ggagatagct atatcgtgat cggagtgggc 600
gagaaaaaga tcacacacca ctggcacaga agcggcagca ccggaggagg cggaggcgtg 660
agctactctc tgtgcactgc tgccttcacc ttcaccaaaa tccccgccga gacactgcac 720
ggaaccgtga ccgtagaagt gcagtacgct ggcaccgacg gaccctgcaa ggtgcccgcc 780
cagatggccg tggacatgca gacactgacc ccagtgggca gactgatcac agctaacccc 840
gtgatcacag agagcaccga aaactctaaa atgatgcttg agcttgaccc cccttttgga 900
gatagctata tagtgatagg agtaggtgaa aagaagataa ctcaccactg gcatagatcc 960
ggtagcaca 969

<210> SEQ ID NO 2
<211> LENGTH: 51
<212> TYPE: DNA
<213> ORGANISM: Artificial Sequence
<220> FEATURE:
<223> OTHER INFORMATION: lgE signal peptide

<400> SEQUENCE: 2
gattggacat ggattctgtt tctggtggct gccgccacca gagtgcattc t 51

<210> SEQ ID NO 3
<211> LENGTH: 1044
<212> TYPE: DNA
<213> ORGANISM: Artificial Sequence
<220> FEATURE:
<223> OTHER INFORMATION: ENV domain III X 3

<400> SEQUENCE: 3
ggatccgcca ccatggattg gacatggatt ctgtttctgg tggctgccgc caccagagtg 60
cattctggag tgagctatag tctgtgtaca gccgctttta cattcactaa gatcccagcc 120
gaaacccttc acggaacagt gacagtggaa gtgcagtacg ctggaactga cggaccatgt 180
aaggtgccag ctcagatggc cgtggatatg caaacactga cacccgtggg aagactgatc 240
acagctaatc cagtgattac tgaatctaca gagaatagca aaatgatgct ggaacttgac 300
cccccatttg gagactcata tattgtgatc ggcgtgggcg agaagaagat cacccaccac 360
tggcatagat ccggcagcac ggggggcggc ggaggcgtga gctacagcct gtgcaccgcc 420
gccttcacct ttaccaagat cccagccgag acgctgcacg gcacagtgac cgtggaggtg 480

-continued

```
cagtacgccg gaaccgacgg accatgcaag gtgccagccc agatggctgt ggacatgcag    540

accctgaccc ccgtgggcag actgatcacc gccaacccag tgatcacaga gtctaccgag    600

aacagcaaga tgatgctgga actggaccca cccttcggag atagctatat cgtgatcgga    660

gtgggcgaga aaaagatcac acaccactgg cacagaagcg gcagcaccgg aggaggcgga    720

ggcgtgagct actctctgtg cactgctgcc ttcaccttca ccaaaatccc cgccgagaca    780

ctgcacggaa ccgtgaccgt agaagtgcag tacgctggca ccgacggacc ctgcaaggtg    840

cccgcccaga tggccgtgga catgcagaca ctgaccccag tgggcagact gatcacagct    900

aaccccgtga tcacagagag caccgaaaac tctaaaatga tgcttgagct tgacccccct    960

tttggagata gctatatagt gataggagta ggtgaaaaga agataactca ccactggcat   1020

agatccggta gcacatgact cgag                                          1044
```

<210> SEQ ID NO 4
<211> LENGTH: 2088
<212> TYPE: DNA
<213> ORGANISM: Artificial Sequence
<220> FEATURE:
<223> OTHER INFORMATION: prM + ENV

<400> SEQUENCE: 4

```
ggatccgcca ccatggactg gacctggatt ctgttcctcg tggctgctgc tacaagagtg     60

cacagcgtca ctagacgtgg gagtgcatac tatatgtact tggacagaaa cgatgctggg    120

gaggccatat cttttccaac cacattgggg atgaataagt gttatataca gatcatggat    180

cttggacaca tgtgtgatgc caccatgagc tatgaatgcc ctatgctgga tgagggggtg    240

gaaccagatg acgtcgattg ttggtgcaac acgacgtcaa cttgggttgt gtacggaacc    300

tgccatcaca aaaaaggtga agcacggaga tctagaagag ctgtgacgct cccctcccat    360

tccactagga agctgcaaac gcggtcgcaa acctggttgg aatcaagaga atacacaaag    420

cacttgatta gagtcgaaaa ttggatattc aggaaccctg gcttcgcgtt agcagcagct    480

gccatcgctt ggcttttggg aagctcaacg agccaaaaag tcatatactt ggtcatgata    540

ctgctgattg ccccggcata cagcatcagg tgcataggag tcagcaatag ggactttgtg    600

gaaggtatgt caggtgggac ttgggttgat attgtcttgg aacatggagg ttgtgtcacc    660

gtaatggcac aggacaaacc gactgtcgac atagagctgg ttacaacaac agtcagcaac    720

atggcggagg taagatccta ctgctatgag gcatcaatat cagacatggc ttcggacagc    780

cgctgcccaa cacaaggtga agcctacctt gacaagcaat cagacactca atatgtctgc    840

aaaagaacgt tagtggacag aggctgggga aatggatgtg gactttttgg caaagggagt    900

ctggtgacat gcgctaagtt tgcatgctcc aagaaaatga ccgggaagag catccagcca    960

gagaatctgg agtaccggat aatgctgtca gttcatggct cccagcacag tgggatgatc   1020

gttaatgaca caggacatga aactgatgag aatagagcga aggttgagat aacgcccaat   1080

tcaccaagag ccgaagccac cctgggggt tttggaagcc taggacttga ttgtgaaccg   1140

aggacaggcc ttgacttttc agatttgtat tacttgacta tgaataacaa gcactggttg   1200

gttcacaagg agtggttcca cgacattcca ttaccttggc acgctggggc agacaccgga   1260

actccacact ggaacaacaa agaagcactg gtagagttca aggacgcaca tgccaaaagg   1320

caaactgtcg tggttctagg gagtcaagaa ggagcagttc acacggccct tgctggagct   1380

ctggaggctg agatggatgg tgcaaaggga aggctgtcct ctggccactt gaaatgtcgc   1440

ctgaaaatgg ataaacttag attgaagggc gtgtcatact ccttgtgtac cgcagcgttc   1500
```

```
acattcacca agatcccggc tgaaacactg cacgggacag tcacagtgga ggtacagtac   1560

gcagggacag atggaccttg caaggttcca gctcagatgg cggtggacat gcaaactctg   1620

accccagttg ggaggttgat aaccgctaac cccgtaatca ctgaaagcac tgagaactct   1680

aagatgatgc tggaacttga tccaccattt ggggactctt acattgtcat aggagtcggg   1740

gagaagaaga tcacccacca ctggcacagg agtggcagca ccattggaaa agcatttgaa   1800

gccactgtga gaggtgccaa gagaatggca gtcttgggag acacagcctg ggactttgga   1860

tcagttggag gcgctctcaa ctcattgggc aagggcatcc atcaaatttt tggagcagct   1920

ttcaaatcat tgtttggagg aatgtcctgg ttctcacaaa ttctcattgg aacgttgctg   1980

atgtggttgg gtctgaacac aaagaatgga tctatttccc ttatgtgctt ggccttaggg   2040

ggagtgttga tcttcttatc cacagccgtc tctgctgatt agctcgag                2088
```

<210> SEQ ID NO 5
<211> LENGTH: 1590
<212> TYPE: DNA
<213> ORGANISM: Artificial Sequence
<220> FEATURE:
<223> OTHER INFORMATION: ENV

<400> SEQUENCE: 5

```
ggatccgcca ccatggactg gacctggatt ctgttcctcg tggctgctgc tacaagagtg     60

cacagcatca ggtgcatagg agtcagcaat agggactttg tggaaggtat gtcaggtggg    120

acttgggttg atattgtctt ggaacatgga ggttgtgtca ccgtaatggc acaggacaaa    180

ccgactgtcg acatagagct ggttacaaca acagtcagca acatggcgga ggtaagatcc    240

tactgctatg aggcatcaat atcagacatg gcttcggaca gccgctgccc aacacaaggt    300

gaagcctacc ttgacaagca atcagacact caatatgtct gcaaaagaac gttagtggac    360

agaggctggg gaaatggatg tggacttttt ggcaaaggga gtctggtgac atgcgctaag    420

tttgcatgct ccaagaaaat gaccgggaag agcatccagc cagagaatct ggagtaccgg    480

ataatgctgt cagttcatgg ctcccagcac agtgggatga tcgttaatga cacaggacat    540

gaaactgatg agaatagagc gaaggttgag ataacgccca attcaccaag agccgaagcc    600

accctggggg gttttggaag cctaggactt gattgtgaac cgaggacagg ccttgacttt    660

tcagatttgt attacttgac tatgaataac aagcactggt tggttcacaa ggagtggttc    720

cacgacattc cattaccttg gcacgctggg gcagacaccg gaactccaca ctggaacaac    780

aaagaagcac tggtagagtt caaggacgca catgccaaaa ggcaaactgt cgtggttcta    840

gggagtcaag aaggagcagt tcacacggcc cttgctggag ctctggaggc tgagatggat    900

ggtgcaaagg gaaggctgtc ctctggccac ttgaaatgtc gcctgaaaat ggataaactt    960

agattgaagg gcgtgtcata ctccttgtgt accgcagcgt tcacattcac caagatcccg   1020

gctgaaacac tgcacgggac agtcacagtg gaggtacagt acgcagggac agatggacct   1080

tgcaaggttc cagctcagat ggcggtggac atgcaaactc tgaccccagt tgggaggttg   1140

ataaccgcta accccgtaat cactgaaagc actgagaact ctaagatgat gctggaactt   1200

gatccaccat ttggggactc ttacattgtc ataggagtcg gggagaagaa gatcacccac   1260

cactggcaca ggagtggcag caccattgga aaagcatttg aagccactgt gagaggtgcc   1320

aagagaatgg cagtcttggg agacacagcc tgggactttg gatcagttgg aggcgctctc   1380

aactcattgg gcaagggcat ccatcaaatt tttggagcag ctttcaaatc attgtttgga   1440
```

-continued

```
ggaatgtcct ggttctcaca aattctcatt ggaacgttgc tgatgtggtt gggtctgaac   1500

acaaagaatg gatctatttc ccttatgtgc ttggccttag ggggagtgtt gatcttctta   1560

tccacagccg tctctgctga ttagctcgag                                    1590


<210> SEQ ID NO 6
<211> LENGTH: 390
<212> TYPE: DNA
<213> ORGANISM: Artificial Sequence
<220> FEATURE:
<223> OTHER INFORMATION: ENV domain III expressing vactor

<400> SEQUENCE: 6

ggatccgcca ccatggactg gacctggatt ctgttcctcg tggctgctgc tacaagagtg     60

cacagcggcg tgtcatactc cttgtgtacc gcagcgttca cattcaccaa gatcccggct    120

gaaacactgc acgggacagt cacagtggag gtacagtacg cagggacaga tggaccttgc    180

aaggttccag ctcagatggc ggtggacatg caaactctga ccccagttgg gaggttgata    240

accgctaacc ccgtaatcac tgaaagcact gagaactcta agatgatgct ggaacttgat    300

ccaccatttg gggactctta cattgtcata ggagtcgggg agaagaagat cacccaccac    360

tggcacagga gtggcagcac ctagctcgag                                     390


<210> SEQ ID NO 7
<211> LENGTH: 315
<212> TYPE: DNA
<213> ORGANISM: Artificial Sequence
<220> FEATURE:
<223> OTHER INFORMATION: ENV domain III

<400> SEQUENCE: 7

ggcgtgtcat actccttgtg taccgcagcg ttcacattca ccaagatccc ggctgaaaca     60

ctgcacggga cagtcacagt ggaggtacag tacgcaggga cagatggacc ttgcaaggtt    120

ccagctcaga tggcggtgga catgcaaact ctgaccccag ttgggaggtt gataaccgct    180

aaccccgtaa tcactgaaag cactgagaac tctaagatga tgctggaact tgatccacca    240

tttggggact cttacattgt cataggagtc ggggagaaga agatcaccca ccactggcac    300

aggagtggca gcacc                                                     315


<210> SEQ ID NO 8
<211> LENGTH: 34
<212> TYPE: DNA
<213> ORGANISM: Artificial Sequence
<220> FEATURE:
<223> OTHER INFORMATION: prME_Pstl_F

<400> SEQUENCE: 8

acaagagtgc acagcgtcac tagacgtggg agtg                                 34


<210> SEQ ID NO 9
<211> LENGTH: 36
<212> TYPE: DNA
<213> ORGANISM: Artificial Sequence
<220> FEATURE:
<223> OTHER INFORMATION: prME_Pstl_R

<400> SEQUENCE: 9

cctctagact cgagctaatc agcagagacg gctgtg                               36


<210> SEQ ID NO 10
<211> LENGTH: 33
```

-continued

```
<212> TYPE: DNA
<213> ORGANISM: Artificial Sequence
<220> FEATURE:
<223> OTHER INFORMATION: E_Pstl_F

<400> SEQUENCE: 10

acaagagtgc acagcatcag gtgcatagga gtc                               33


<210> SEQ ID NO 11
<211> LENGTH: 33
<212> TYPE: DNA
<213> ORGANISM: Artificial Sequence
<220> FEATURE:
<223> OTHER INFORMATION: ED3 domain III_Pstl_F

<400> SEQUENCE: 11

acaagagtgc acagcggcgt gtcatactcc ttg                               33


<210> SEQ ID NO 12
<211> LENGTH: 35
<212> TYPE: DNA
<213> ORGANISM: Artificial Sequence
<220> FEATURE:
<223> OTHER INFORMATION: ED3 domain III_Pstl_R

<400> SEQUENCE: 12

cctctagact cgagctaggt gctgccactc ctgtg                             35


<210> SEQ ID NO 13
<211> LENGTH: 30
<212> TYPE: DNA
<213> ORGANISM: Artificial Sequence
<220> FEATURE:
<223> OTHER INFORMATION: ED3 domain IIIx3_BHI_F

<400> SEQUENCE: 13

taccgagctc ggatccgcca ccatggattg                                   30


<210> SEQ ID NO 14
<211> LENGTH: 28
<212> TYPE: DNA
<213> ORGANISM: Artificial Sequence
<220> FEATURE:
<223> OTHER INFORMATION: ED3 domain IIIx3_Xhol_R

<400> SEQUENCE: 14

gccctctaga ctcgagtcat gtgctacc                                     28
```

RECOMBINANT ANTIGEN DERIVED FROM ZIKA VIRUS E PROTEIN AND USE THEREOF

TECHNICAL FIELD

The present invention relates to a recombinant antigen derived from Zika virus E protein and use thereof. More particularly, the present invention relates to a recombinant antigen comprising a sequence of domain III of Zika virus envelope protein ("E") or a repeated sequence thereof, a DNA vaccine composition for the prevention of Zika virus using the recombinant antigen, a neutralizing antibody against Zika virus produced using the recombinant antigen.

CROSS-REFERENCE TO SEQUENCE LISTING

The Sequence Listing identified as "CNP0018-00US_SeqList_ST25.txt" (11,010 bytes), created Nov. 15, 2021, is hereby incorporated by reference.

BACKGROUND ART

Zika virus (also briefly referred to as "ZIKV") is a new virus that was found in Rhesus monkeys in 1947 in Uganda and transmitted by mosquitoes, and was also found in human in 1952 in Uganda and the United Republic of Tanzania. Thereafter, sporadic outbreaks of the Zika virus disease have been reported in some countries of Africa, Southeast Asia, but it had not become an object of great interest. Since the large outbreaks of the viral disease were reported in 2007 on the Yap Islands, the viral disease has spread to several island countries in the Pacific. The viral disease, since 2015, has spread to several countries in the Continent of America, mainly Brazil, and the outbreaks of the viral disease have continued to the present time in many countries of Central and South America.

It was found that Zika virus could be transmitted from a pregnant woman to her fetus, and there was a report on serious birth defects in the brain called microcephaly in the actual liveborn infant. Since then, the WHO has declared that Zika virus constitutes a public health emergency of international concern.

When Zika virus causes a disease in human, self-limited febrile illness occurs which manifests as slight fever, rash, headache, conjunctivitis, myalgia, and arthralgia. Recently, it was found that the infection of Zika virus is associated with an increased incidence of microcephaly in fetuses and infants, and Guillain-Barré syndrome in adults. The latency period of a Zika virus disease is not known exactly, but it is estimated to range from a few days to a week. Generally its symptoms are mild and usually last for a few days to a week. Zika virus generally remains in the blood of infected people for about a week, but among some people Zika virus may remain for a longer period.

Currently, there are no prophylactic vaccines or therapeutic agents for the prevention of the infection of Zika virus. Although symptoms associated with the infection of Zika virus are generally mild, an infection during pregnancy can cause the outbreak of microcephaly in fetus, and there are also very fetal threats, such as the outbreak of Guillain-Barré syndrome that may cause paralysis. Therefore, there is a need for the development of a safe vaccine that leads to an immune response for protecting against a Zika virus disease.

Zika virus is a positive-sense, single-stranded RNA virus belonging to the Flavivirus genus, Flaviviridae family Zika virus has a RNA genome of about 11 kilobases in length that encodes three structural proteins, Capsid ("C"), Precursor Membrane ("prM"), and Envelope ("E") proteins, and seven non-structural proteins (NS1, NS2A, NS2B, NS3, NS4A, NS4B, and NS5).

In order to develop a virus vaccine, attempts have been made to develop a purified killed vaccine, an attenuated live vaccine, a recombinant subunit vaccine, an adenoviral vector vaccine, a virus-like particle (VLP), and a DNA or RNA vaccine and the like. Among them, an attenuated live vaccine (live attenuated virus, LAV) has been used for a long time as an efficient vaccine. LAV is thought to be suitable for generating an immune response because it is derived from pathogens that cause a disease, but is intentionally weakened at a laboratory. Currently, oral polio vaccine, measles vaccine, rotavirus vaccine, and yellow fever vaccine and the like are sold as vaccines in form of LAY. However, there are still safety issues, such as reversion, purity, and potential contamination in a virus agent used in LAV vaccine and the like.

The DNA vaccines have many advantages over the conventional vaccines. The DNA vaccines can utilize the whole antigen required for inducing an immune response in a gene form, which can lead to a wide range of immune responses. In addition, the DNA vaccine is also safer than other vaccines that include whole infectious agents, since the DNA vaccine includes only antigen genes that are designed to be modified for multi-genes or repeated domains, and thereby increases antigenicity. Furthermore, it is possible to insert multiple antigens into one plasmid DNA, which facilitates the design and construction of antigens. It can be easily mass-produced using *E. coli* as a host cell. Since the plasmid DNA is a very stable high molecular substance, it is characterized in that it can be stored for a long period even at room temperature in comparison with other vaccines.

On the other hand, several previous studies related to a Zika virus vaccine have been based on a purified killed vaccine, or have used the whole Zika virus E protein as an antigen. For example, European Patent No. 3184118 includes a portion encoding the prM protein, including the E protein base sequence as an antigen, and uses a vector derived from a virus. In addition, in Korean Patent Publication No. 10-2018-0036987, an antigen of Zika virus is an inactivated whole virion, or the Zika virus vaccine comprises an E protein, an M protein, and optionally a non-structural 1 (NS1) protein as an antigen. However, DNA vaccines that are based on the repeated use of only a partial domain of the E protein have not been disclosed to the present time.

DISCLOSURE OF INVENTION

Technical Problem

It is an object of the present invention to provide an effective DNA vaccine for increasing the expression of an antigen and inducing a high antibody titer and preventing the infection of Zika virus by using Zika virus E protein domain III.

In addition, it is another object of the present invention to provide a neutralizing antibody that can be used for the prevention or treatment of the infection of Zika virus.

Solution to Problem

The present invention provides a polynucleotide of SEQ ID NO: 1 encoding Zika virus E protein domain III repeatedly three times. The present invention also provides a polynucleotide of SEQ ID NO: 7 encoding Zika virus E protein domain III. In a preferred embodiment, the polynucleotide may further comprise a polynucleotide of SEQ ID NO: 2 encoding an IgE signal peptide.

The present invention provides a recombinant expression vector comprising the polynucleotide. Preferably, the recombinant expression vector is a recombinant expression vector (pVAX1-ENV domain III×3) having a base sequence of SEQ ID NO: 3 or SEQ ID NO: 6. In one embodiment, the vector may be a plasmid, but is not limited to thereto.

In addition, the present invention provides an isolated host cell comprising the polynucleotide or recombinant expression vector. In one certain embodiment, the host cell is *E. coli*-DH5α, which comprises a pVAX1-ENV domain III×3 recombinant expression vector and was deposited as an accession number KCTC13685BP.

In addition, the present invention provides a DNA vaccine composition for the prevention of the infection of Zika virus, comprising the polynucleotide or recombinant expression vector as an active ingredient.

Specifically, the present invention relates to a vaccine composition for the prevention of the infection of Zika virus, comprising a polynucleotide of SEQ ID NO: 1 encoding Zika virus E protein domain III repeatedly three times or a polynucleotide of SEQ ID NO: 7 encoding Zika virus E protein domain III. Preferably, the vaccine composition may further comprise the polynucleotide and a polynucleotide of SEQ ID NO: 2 encoding an IgE signal peptide.

The present invention relates to a vaccine composition for the prevention of the infection of Zika virus, comprising a recombinant expression vector having a base sequence of SEQ ID NO: 3 or SEQ ID NO: 6.

In addition, the vaccine composition of the present invention may further comprise an adjuvant.

The vaccine composition of the present invention induces an immune response to Zika virus by expressing a Zika virus antigen protein.

The present invention also relates to a method for preparing a neutralizing antibody against Zika virus, comprising (a) a step of administering the polynucleotide to a mammalian excluding a human; and (b) a step of obtaining a neutralizing antibody that specifically binds to Zika virus from the mammalian, and a neutralizing antibody produced therefrom. The method may further comprise (c) a step of humanizing the neutralizing antibody obtained in step (b).

Effect of the Invention

The DNA vaccine composition according to the present invention enhances the antigen expression rate by comprising a codon-optimized antigen gene of Zika virus E protein domain III, and thereby induces an effective antigen-specific antibody response, a neutralizing antibody response, a cell-mediated immune response showing a high IFN-γ production in splenocytes of an animal model.

In particular, the DNA vaccine composition according to the present invention shows greatly superior effects in comparison with the conventional vaccine in which whole prME antigen is expressed.

Therefore, the DNA vaccine composition according to the present invention can be effectively used for the prevention of the infection of Zika virus.

In addition, the polynucleotide comprising a codon-optimized antigen gene of Zika virus E protein domain III according to the present invention can be also used for the production of a neutralizing antibody for the prevention or treatment of the infection of Zika virus and for the detection of Zika virus.

DETAILED DESCRIPTION OF THE INVENTION

1. Polynucleotide

Figure 1:
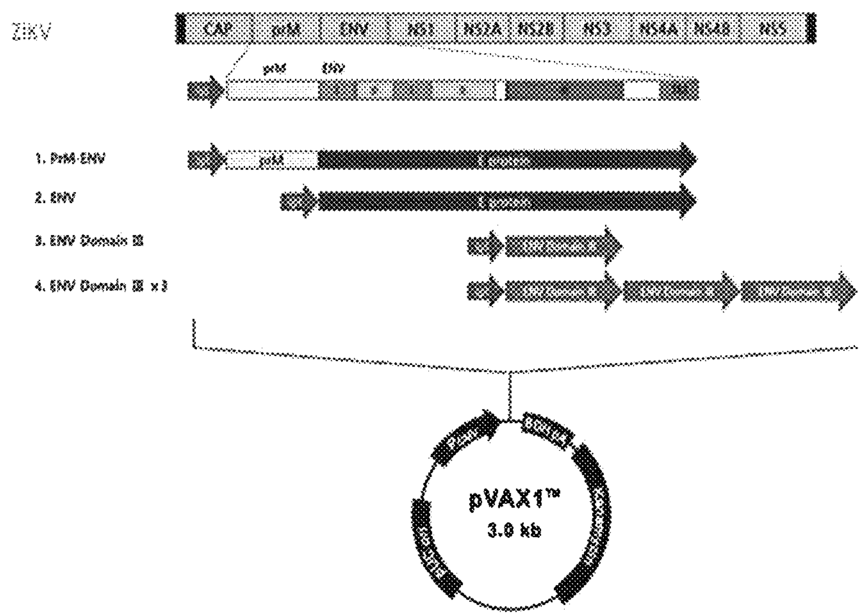
FIG. 1 illustrates a diagram of a plasmid construct for preparing Zika virus (ZIKV) DNA vaccine candidates used in Example 1. A gene encoding the prM or E protein of the ZIKV sequence and a gene encoding the IgE signal peptide are introduced into the pVAX1 mammalian expression vector.

The present invention relates to a polynucleotide of SEQ ID NO: 1 encoding Zika virus E protein domain III repeatedly three times. The present invention also provides a polynucleotide of SEQ ID NO: 7 encoding Zika virus E protein domain III. In a preferred embodiment, the polynucleotide may further comprise a polynucleotide of SEQ ID NO: 2 encoding an IgE signal peptide.

In the present invention, Zika virus E protein domain III is selected as an antigen of a Zika virus vaccine. The Zika virus E protein (envelope protein) mediates virus assembly, attachment to cell receptors, and is necessary for subsequent membrane fusion associated with virus entry. The Zika virus E protein consists of three (3-sheet domains. Among them, domain III includes a cell receptor binding motif. In particular, domain III is mapped with a type-specific neutralizing epitope that induces a strong host antibody response or protective immunity.

In order to use the selected Zika virus E protein domain III as an antigen of a DNA vaccine, it is necessary to efficiently express a gene derived from a virus in a mammalian. For this purpose, polynucleotides may be substituted with a codon having a high expression frequency in a host cell. The expression "substituting with a codon having a high expression frequency in a host cell" or "codon optimization," as used in the present invention, refers to substituting with the codon having a high preference, and thus increasing the expression efficiency of the amino acid or protein that is encoded by the nucleic acids, since there is a codon having high preference depending on hosts among codons designating the amino acids upon transcription and translation of DNA to a protein in a host cell.

In the present invention, the polynucleotide of the natural type Zika virus E protein domain III was used in a suitable form for expression in a mammalian by codon optimization (SEQ ID NO: 7), or was prepared so as to have a three-fold repeated structure after codon optimization (SEQ ID NO: 1). For example, the Kazusa program (www.kazusa.orjp/codon/) may be used for the codon optimization.

In accordance with a preferred embodiment of the present invention, the codon optimized polynucleotide may further comprise a polynucleotide that is linked to its N-terminus and encodes an IgE signal peptide. The term "signal peptide," as used herein, refers to a peptide that plays a role in transferring the E protein domain III expressed in a cell to outside of the cell. Generally, when an antigen protein produced in a DNA vaccine is secreted out of a cell, a more effective immune response can be obtained by inducing the production of an antigen specific IgG in a larger amount in comparison with being placed inside of a cell (cytosol) or on a cellular membrane.

In the present invention, by linking the polynucleotide of SEQ ID NO: 2 encoding the IgE signal peptide to a N-terminus portion of the codon optimized polynucleotide of SEQ ID NO: 1 or SEQ ID NO: 7, Zika virus E protein domain III expressed in a cell may be induced to transfer to outside of the cell.

The polynucleotide may further comprise a polynucleotide encoding one or more immunity enhancing peptides. The term "immunity enhancing peptide," as used herein, refers to a peptide that activates cells (for example, dendritic cells and the like) involved in the immune response to increase the immune response. The peptides known in the art can be used as the immunity enhancing peptide, and the peptides known in the art may be, for example, CD40 ligand, Flt3 (fins-like tyrosine kinase-3) ligand, flagellin, or CTLA4 (cytotoxic T lymphocyte associated protein 4) and the like.

Methods for obtaining the polynucleotide of the present invention are known in the art. For example, polynucleotide molecules can be prepared directly through a chemical synthesis.

2. Recombinant Expression Vector

The present invention provides a recombinant expression vector comprising the polynucleotide.

The vector according to one embodiment of the present invention may be an expression vector in which the polynucleotide comprises a gene construct operably linked to a regulatory sequence so that it can express Zika virus E protein domain III in a host cell. The expression vector may be a plasmid vector, a viral vector, a cosmid vector, a phagemid vector, or an artificial human chromosome.

"Operably linked to" means that the desired nucleic acid sequence is linked to a regulatory sequence so as to perform the expression.

Regulatory sequences may be promoters, enhancers, initiation codons, stop codons, or polyadenylation signals. Regulatory sequences include directing the expression of the nucleic acid of interest in many host cells at all times, directing the expression of the nucleic acid of interest only in a certain tissue cell (e.g., a tissue-specific regulatory sequence), and directing the expression to be induced by a certain signal (e.g., inducible regulatory sequences). The design of the expression vector may vary depending on factors, such as the selection of a host cell to be transformed and the expression level of the desired protein.

In a preferred embodiment, the expression vector is a plasmid vector, more preferably, pVAX1™ (Invitrogen, San Diego, Calif.) expression plasmid. This expression vector is to be modified by substituting the high copy pUC replication origin with the low copy pMB1 replication origin of pBR322. The low copy modification was performed to make the construct more stable by reducing the metabolism burden.

In the present invention, pVAX1 is used as an expression vector backbone, and a polynucleotide encoding Zika virus E protein domain III repeatedly three times is inserted into the vector to produce the expression plasmid "pVAX1-ENV domain III×3." The plasmid pVAX1-ENV domain III×3 construct is illustrated in FIG. 1, and has the base sequence described in SEQ ID NO: 3. As in the same manner, the polynucleotide encoding Zika virus E protein domain III is inserted into the vector to produce the expression plasmid, which has the base sequence of SEQ ID NO: 6.

The vectors of the present invention can be prepared by standard recombinant DNA techniques. The standard recombinant DNA techniques include, for example, blunt end and adhesive end ligation, restriction enzyme treatment to provide appropriate ends, removal of phosphate groups by alkaline phosphatase treatment to prevent an unsuitable binding, and an enzymatic linkage by T4 DNA ligase and the like. DNA encoding the IgE signal peptide obtained by chemical synthesis or genetic recombination technique, DNA encoding Zika virus E protein domain III of the present invention repeatedly three times, is recombined into a vector comprising an appropriate regulatory sequence, thereby the vector of the present invention can be produced. The vector comprising the regulatory sequence can be commercially purchased or manufactured. In one embodiment of the present invention, pVAX1, which is a vector for producing a DNA vaccine, was prepared and used.

3. Host Cell

The present invention relates to an isolated host cell comprising the vector.

The term "host cell," as used herein, includes prokaryotic or eukaryotic cells, and eukaryotic cells include lower eukaryotic cells including fungi, yeast and the like, as well as higher eukaryotic cells including mammalian and the like. Suitable prokaryotic cells are those cells commonly used for cloning, such as *E. coli* or *Bacillus subtilis*. In addition, eukaryotic cells include fungal cells, plant cells, or animal cells. Examples of suitable fungal cells may be yeast, preferably yeast belonging to the genus *Saccharomyces* sp. Examples of suitable animal cells may include insect cells, plant cells, preferably mammalian cells such as HEK293, 293T, NSO, CHO, MDCK, U2-OSHela, NIH3T3, MOLT-4, Jurkat, PC-12, PC-3, IMR, NT2N, Sk-n-sh, CaSki, and C33A.

A host cell transfected or transformed with the vector according to one embodiment of the present invention may be a host cell genetically modified by the vector. The term "genetically modified," as used herein, means that a host cell comprises a polynucleotide or vector introduced into a host cell other than its genome. Furthermore, the polynucleotide or vector according to one embodiment of the present invention may be present in a genetically modified host cell as an independent molecule outside the genome, preferably as a replicable molecule, or may be stably inserted into the genome of the host cell.

In a preferred embodiment of the present invention, the host cell is *E. coli*. More preferably, the host cell is *E. coli*-DH5α, which comprises the recombinant expression vector pVAX1-ENV domain III×3 and is deposited as an accession number KCTC13685BP.

4. DNA Vaccine Composition

The present invention relates to a DNA vaccine composition comprising the polynucleotide or the recombinant expression vector as an active ingredient.

The term "DNA vaccine," as used herein, a vaccine platform in which a gene encoding an antigen that induces an immune response in order to prevent and treat a disease caused by a pathogenic infection is inserted into a purified plasmid vector, and is injected in vivo, and the antigen expressed in protein/peptide form through the transcription and translation process in a host system simultaneously induces cellular and humoral immune responses.

Plasmids used in DNA vaccines have promoter sequences that can strongly express antigen proteins in animal cells, and use shuttle vectors that are applicable to both animal cells and bacteria to amplify plasmids in a large amount in bacteria. Plasmid DNA, which is amplified in a large amount in bacteria, separated and purified, is injected into cells, transcribed in the cell nucleus, and translated in the cytoplasm to express the desired antigen protein/peptide.

When the antigen protein/peptide expressed in the cell is broken down into a small peptide in the cytoplasmic proteasome, it is bound to the major histocompatibility complex (MHC) class I molecule in the Golgi complex and presented on the cell surface, which is recognized by CD8+ cytotoxic T cells to induce cellular immunity. When the antigen protein expressed in vivo is captured in B cells or macrophages, which are antigen presenting cells in the body, it is bound to MHC class II molecules in intracellular lysosomes and presented on the cell surface, which is recognized by CD4+ helper T cells to activate the humoral immune response. In addition, B cells that recognize the antigen protein are activated to produce antigen specific antibodies.

In addition, the vaccine composition of the present invention induces a neutralizing antibody of high titer. In one embodiment, the vaccine composition of the present invention induces a neutralizing antibody of higher titer than when using a polynucleotide that encodes a structural protein of Zika virus, for example, the E protein and/or prM. Therefore, the vaccine composition of the present invention shows an effective neutralizing antibody response.

In accordance with one embodiment of the present invention, the DNA vaccine composition of the present invention may further comprise one or more pharmaceutically acceptable carriers or excipients. Pharmaceutically acceptable carriers include, for example, carriers for parenteral administration, such as water, suitable oil, saline, aqueous glucose, and glycol and the like, and may further include stabilizers and preservatives. Suitable stabilizers include antioxidants such as sodium hydrogen sulfite, sodium sulfite, or ascorbic acid. Suitable preservatives include benzakonium chloride, methyl- or propyl-paraben, and chlorobutanol.

In addition, the composition according to the present invention may adequately comprise suspending agents, solubilizing agents, stabilizers, isotonic agents, preservatives, anti-adsorption agents, surfactants, diluents, excipients, pH adjusters, analgesic agents, buffers, antioxidants, and the like depending on administration methods or formulations, if necessary.

In accordance with one embodiment of the present invention, the DNA vaccine composition of the present invention may comprise at least one or more pharmaceutically acceptable adjuvants or immunity enhancers. The term "adjuvant" or "immunity enhancer," as used herein, refers to a pharmaceutical or immunological preparation to be administered for enhancing an immune response of a vaccine. The adjuvant may be aluminium hydroxide, aluminium phosphate, alum (potassium aluminium sulfate), MF59, virosome, AS04 [a mixture of aluminium hydroxide and monophosphoryl lipid A (MPL)], AS03 (a mixture of DL-α-tocopherol, squalene, and polysorbate 80, which is an emulsifying agent), CpG, Flagellin, Poly I:C, AS01, AS02, ISCOMs, or ISCOMMATRIX.

The vaccine composition of the present invention for parenteral administration may comprise antioxidants, buffers, bacteriostatic agents, and aqueous and non-aqueous sterile injection solvents comprising solutes for making a solution condition isotonic to blood of an intended recipient and the like, and aqueous and non-aqueous sterile suspensions may include suspending agents and thickening agents. Additives that are useful for utilizing as a solvent for injection include, for example, water, alcohol, polyol, glycerin, and vegetable oil and the like. The composition may provide as a unit dose (one dose) or multiple doses (several doses) container. For example, the composition may provide as a sealed ampoule and vial, and may be stored under freeze dried condition that needs only the addition of sterile liquid carrier, for example, water that is necessary for preparing an injection solution just before use. For example, the administration may be carried out via muscular injection, subcutaneous injection, or intraperitoneal injection.

The vaccine composition of the present invention may be administered with a dose that is properly determined depending on health condition, body weight, sex of a subject to be administered, and administration purpose and the like.

According to one embodiment of the present invention, a polynucleotide that encodes Zika virus E protein domain III that is contained in the DNA vaccine composition of the present invention, or encodes Zika virus E protein domain III repeatedly three times, or a recombinant expression vector comprising the polynucleotide, for example, expression plasmid pVAX1-ENV domain III or pVAX1-ENV domain III X 3 expresses a Zika virus antigen protein in vivo after being injected in vivo, and produces and secretes a Zika virus antigen protein out of a cell. For example, the antigen protein may be produced inside a cell, and then, be transported by a signal peptide to outside of the cell. By the Zika virus antigen protein produced therefrom, an immune response to Zika virus may be induced in vivo.

The term "immune response," as used herein, refers to an activation of immune system of a host, for example, a mammalian in response to an antigen introduction. The immune response may be cellular or humoral response, or both cellular and humoral response. In addition, the immune response may induce the production of a neutralizing antibody.

5. Neutralizing Antibody and Preparation Method Thereof

The present invention provides a neutralizing antibody against Zika virus that is obtained using the polynucleotide, and a method for preparing the neutralizing antibody.

In one embodiment of the present invention, the neutralizing antibody may be obtained by the immunization of a mammalian using the polynucleotide. Specifically, a method for preparing the neutralizing antibody comprises a step of administering the polynucleotide to a mammalian, and a step of obtaining a neutralizing antibody that specifically binds to Zika virus from the mammalian Wherein, the mammalian may be a mammalian excluding a human. For example, the mammalian includes rats, mice, hamsters, pigs, rabbits, horses, donkeys, goats, sheep, guinea pigs, llama and the like, but is not limited thereto. For example, mice may be used to produce monoclonal antibodies, and rabbits or guinea pigs may be used to produce polyclonal antibodies.

In one embodiment of the present invention, the neutralizing antibody produced in a non-human mammalian may be converted to a humanized antibody. In this case, the method of the present invention may further comprise a step of humanizing the neutralizing antibody produced in the non-human mammalian.

The term "humanized antibody," as used herein, is a genetically engineered antibody in which the CDRs from a non-human "donor" antibody are conjugated to a human "recipient" antibody sequence. The recipient antibody sequence may be, for example, a mature human antibody sequence, a complex of such sequences, a common sequence or a germline sequence of a human antibody sequence. Methods for converting from a non-human antibody to a humanized antibody can be performed by methods known in the art.

The neutralizing antibody of the present invention may be used for the prevention or treatment of diseases caused by the infection of Zika virus among mammalians. The neutralizing antibody is used in a sufficient dose to neutralize Zika virus.

Hereinafter, the present invention will be described in more detail with reference to the following examples. However, the following examples are for illustrative purposes only and are not intended to limit the scope of the present invention.

[Example 1] Construction of DNA Vaccine Candidate

The polynucleotide encoding E protein ("ENV") and prM, which are structural proteins of Zika virus (Candidate 1); the polynucleotide encoding E protein (Candidate 2); the polynucleotide encoding E protein domain III (Candidate 3); or the polynucleotide encoding E protein domain III repeatedly three times (Candidate 4) were separately inserted into the pVAX1 vector designed for the purpose of the development of a DNA vaccine, thereby four DNA vaccine candidates were constructed (Table 1 and FIG. 1).

TABLE 1

| DNA Vaccine Candidate | Expression Protein | Polynucleotide of DNA Vaccine Candidate (pVAX1 Vector) |
|---|---|---|
| 1 | prM + ENV | SEQ ID NO: 4 |
| 2 | ENV | SEQ ID NO: 5 |
| 3 | ENV domain III (alone) | SEQ ID NO: 6 |
| 4 | ENV domain III X 3 (repeatedly three times) | SEQ ID NO: 3 |

The domain III portion of the E protein is known to be important for antibody-forming reactions and protective immunity, since it contains a large number of cell receptor attaching motifs in the structural proteins of Zika virus. The domain III portion of the E protein was constructed alone or in a repeated structure by codon optimization so as to be expressed among mammalians (Candidates 3 and 4).

For this purpose, a PCR reaction was carried out using a SPH2015 strain (Brazil Zika virus) clone as a template to amplify each protein gene of Candidates 1 to 3. Wherein the polynucleotide having the base sequence of SEQ ID NO: 7 was used as the polynucleotide that encodes the E protein domain III in Candidate 3. Forward (F) Primer and Reviser Primer used at that time are shown in Tables 2 to 4.

TABLE 2

| Primer Used in Expression Protein Gene PCR of Candidate 1 | |
|---|---|
| prME_Pstl_F | ACA AGA GTG CAC AGC GTC ACT AGA CGT GGG AGT G |
| prME_Pstl_R | CCT CTA GAC TCG AGC TAA TCA GCA GAG ACG GCT GTG |

TABLE 3

| Primer Used in Expression Protein Gene PCR of Candidate 2 | |
|---|---|
| E_Pstl_F | ACA AGA GTG CAC AGC ATC AGG TGC ATA GGA GTC |
| prME_Pstl_R | CCT CTA GAC TCG AGC TAA TCA GCA GAG ACG GCT GTG |

TABLE 4

| Primer Used in Expression Protein Gene PCR of Candidate 3 | |
|---|---|
| ED3 domain III_Pstl_F | ACA AGA GTG CAC AGC GGC GTG TCA TAC TCC TTG |
| ED3 domain III_Pstl_R | CCT CTA GAC TCG AGC TAG GTG CTG CCA CTC CTG TG |

In case of Candidate 4, the polynucleotide of SEQ ID NO: 1 encoding the E protein domain III repeatedly three times was constructed through the gene synthesis and then amplified by the PCR synthesis using the primer of Table 5.

TABLE 5

| Primer used in expression protein gene PCR of Candidate 4 | |
|---|---|
| ED3 domain IIIx3_BHI_F | TAC CGA GCT CGG ATC CGC CAC CAT GGA TTG |
| ED3 domain IIIx3_Xhol_R | GCC CTC TAG ACT CGA GTC ATG TGC TAC C |

Each DNA vaccine candidate was constructed by linking the polynucleotide encoding the IgE signal peptide (SEQ ID NO: 2) to increase the amount of the expressed antigen. Specifically, pVAX1 vector comprising the IgE signal peptide and Kozak consensus sequence and each of the amplified genes were treated with the same restriction enzyme and ligated to construct each DNA vaccine candidate.

[Example 2] Mouse Immunization

Figure 2:
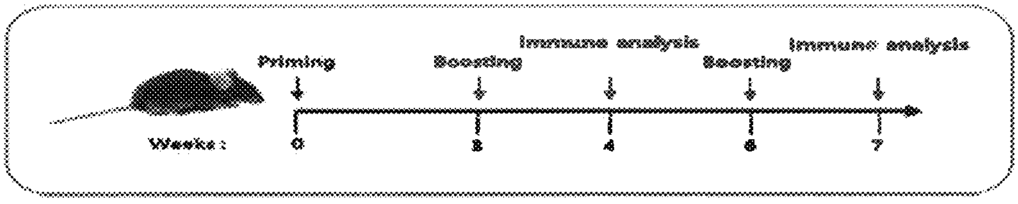
FIG. 2 shows the immunization and immune analysis schedule of mice using DNA vaccine candidates as described in Example 2.

200 μg of each DNA vaccine candidate prepared in Example 1 and aluminium hydroxide as an adjuvant were mixed, and 5-week-old female C57BL/6 mice were immunized by muscle inoculation three times at intervals of 3 weeks. Blood and splenocytes obtained from mice one week after the second and third inoculation were used to analyze cellular immune responses and humoral immune responses. Specific mouse immunization and immune response analysis schedules are shown in FIG. 2.

[Example 3] Analysis of Antigen Specific Antibody Titer Against Zika Virus E Protein Antigen specific antibody titers of vaccine candidates were analyzed using the serum obtained from mice immunized according to Example 2.

50 μl of 1 μg/ml of the E protein derived from Baculovirus was added to each well of ELISA 96-well plate (Nunc Maxisorp; Nunc, 442404) using ELISA coating buffer (Biolegend, 4217), and was coated by reacting at 4° C. overnight. After the reaction, the reaction solution was removed, and washing buffer 1×PBST (0.05% Tween20) was added to each well to wash the cells repeatedly twice, and then, 100 μl of blocking buffer PBS+1% BSA was added to each well, and was blocked by reacting at 37° C. for 2 hours.

As in the same manner, after washing with 1×PBST (0.05% Tween20) repeatedly twice, the immunized mouse serum of Example 2 diluted continuously in a dilution buffer PBS+1% BSA from 100:1 to 2:1 was used as a primary antibody and added to each well in an amount of 50 μl, and reacted at 37° C. for 1 hour. After washing with 1×PBST (0.05% Tween20) repeatedly three times, mouse IgG (Santacruz, sc-2005) conjugated with horseradish peroxidase (HRP) as a secondary antibody was diluted with a dilution buffer PBS+1% BSA to 5000:1 and added to each well in an amount of 50 μl, followed by reacting at 37° C. for 1 hour. After washing with 1×PBST (0.05% Tween20) repeatedly five times, 50 μl of the coloring reagent TMB was added to each well, followed by reacting at room temperature for 10 minutes. The reaction was stopped by adding 100 μl of the stop solution (GenDEPOT, T3550-100) to each well, and then, the absorbance was measured at 450 nm with an ELISA reader. The results are shown in FIG. 3.

Figure 3:
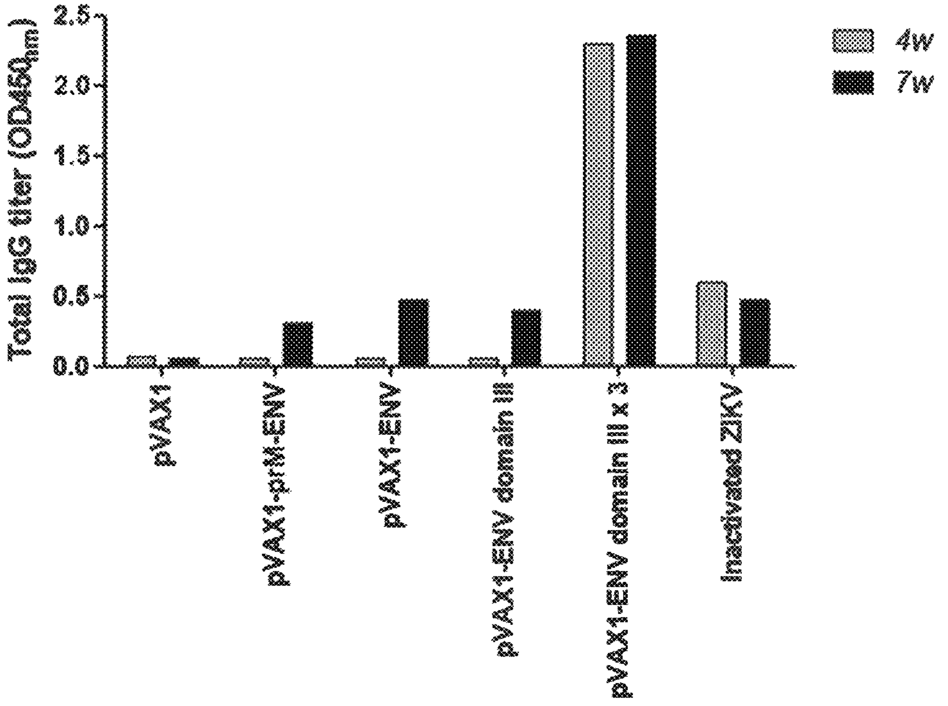
FIG. 3 shows the results of the measurement of an antigen-specific antibody titer (total IgG) against Zika virus E protein induced by a DNA vaccine candidate through ELISA.

As shown in FIG. 3, it was confirmed that all of the Vaccine Candidates 1 to 4 exhibited antibody titer at Week 7, which was one week after the third inoculation. In particular, Candidate 4 (pVAX1-ENV domain III X 3 vaccine candidate) showed a significantly higher antibody titer than the other vaccine candidates by 5 times or more, and a sufficient antibody titer was induced only by the second inoculation (FIG. 3).

[Example 4] Analysis of Specific IgG Subtype for Zika Virus E Protein

The subtypes of anti-Zika virus IgG antibodies formed in the immunized mice were analyzed using the serum of mice collected at Week 7 after inoculation with the vaccine candidates of Example 2.

The same ELISA analysis as used in Example 3 was used except that each subtype antibody of mouse IgG of Table 6 was used as a secondary antibody.

TABLE 6

| Subtype | Manufacturer (Southern Biotech) Catalog No. |
|---|---|
| IgG1 | 1071-05 |
| IgG2a | 1081-05 |
| IgG2b | 1091-05 |
| IgG3 | 1101-05 |

Figure 4:
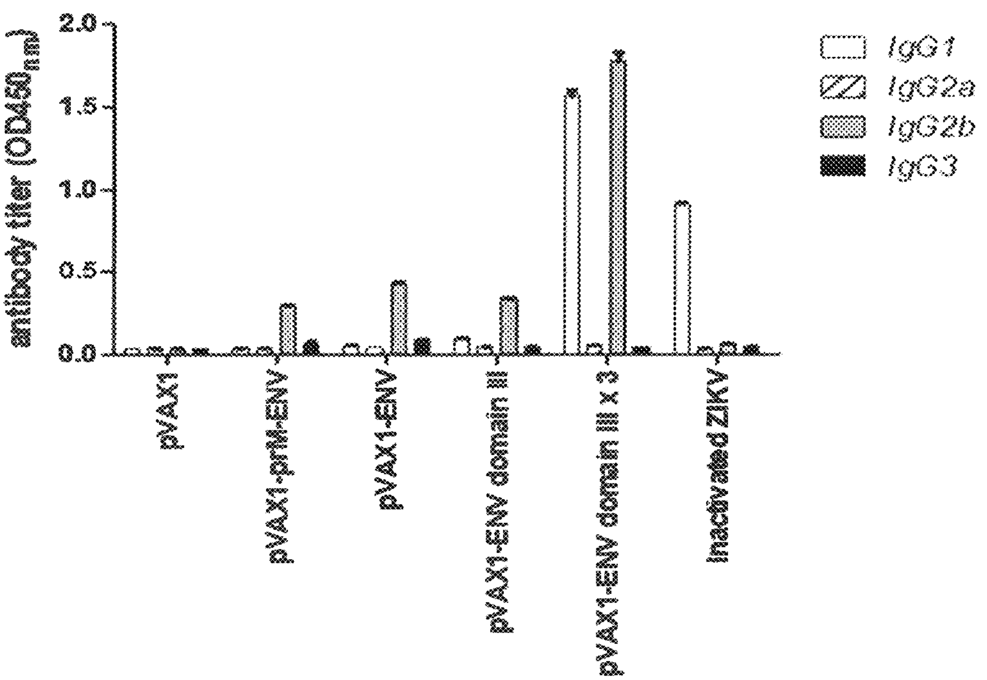
FIG. 4 shows the results of the analysis of a subtype of IgG antibody (IgG subtype) against a Zika virus E protein induced by a DNA vaccine candidate.

As a result, as shown in FIG. 4, IgG2b antibody production ability was high in Candidates 1 to 3 (prM-ENV, ENV, and ENV domain III). On the other hand, in case of Candidate 4 (ENV domain III X 3), it was confirmed that both of IgG2b and IgG1 antibody production abilities were high.

[Example 5] Analysis of Neutralizing Antibody Titer

Neutralizing antibody titers of the vaccine candidates were analyzed using the serum obtained from the mice immunized according to Example 2.

Serum neutralization analysis was carried out in 96-well plates comprising confluent Vero cells seeded 24 hours prior to an analysis. Serum samples, which were two-fold serially diluted in the same volume, were mixed with 50 μl of 100 TCID50 Zika virus (strain MR766, African line) and incubated at 37° C. for 1 hour. The mixture was applied to a monolayer of Vero cells and incubated at 37° C. for 5 days. The neutralizing antibody titer was determined as the highest-order dilution with no cytopathic effect (CPE), and the results are shown in FIG. 5.

Figure 5:
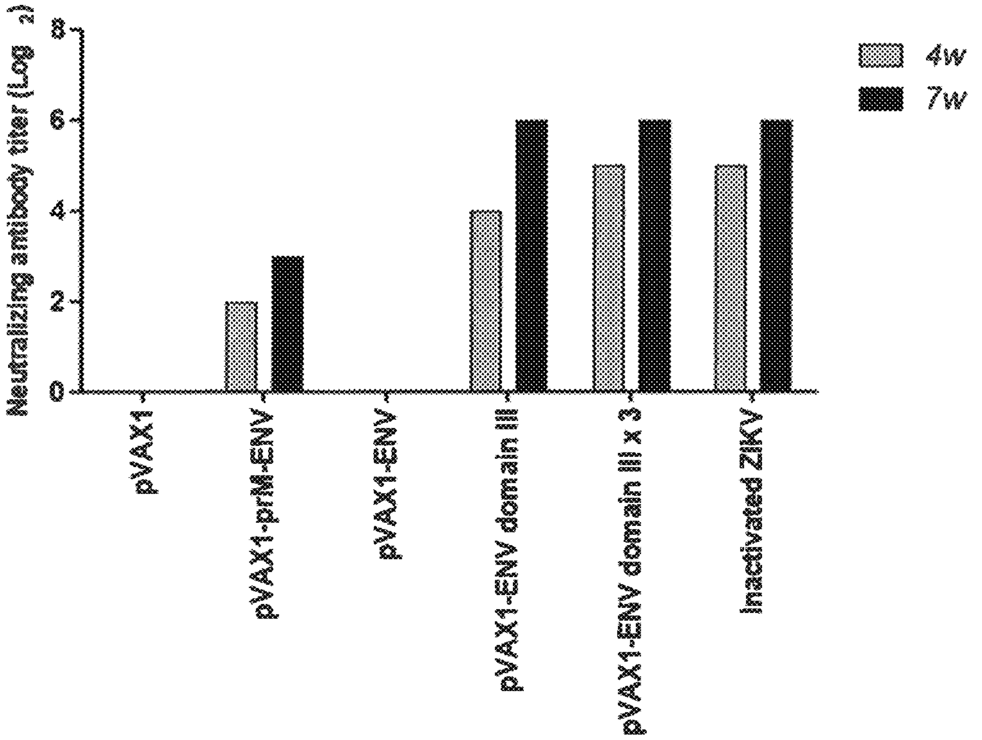
FIG. 5 shows the results of the measurement of serum neutralizing antibody response to Zika virus strain MR766 induced by a DNA vaccine candidate.

As shown in FIG. 5, it was confirmed that Candidates 3 and 4 (vaccine candidates that express ENV domain III alone or repeatedly) had a higher neutralizing antibody titer than Candidate 1 (vaccine candidate that expresses prM-ENV).

[Example 6] Cellular Immune Response Analysis

The antigen specific T cell response was analyzed using splenocytes obtained from mice by the third inoculation of the DNA vaccine candidates in Example 2.

The separated splenocytes were stimulated with 1 μg/ml of Zika virus pepmix (JPT), which consists of 146 mixtures of 15-mer peptides constituting the E protein of Zika virus, at 37° C. for 24 hours.

Figure 6:
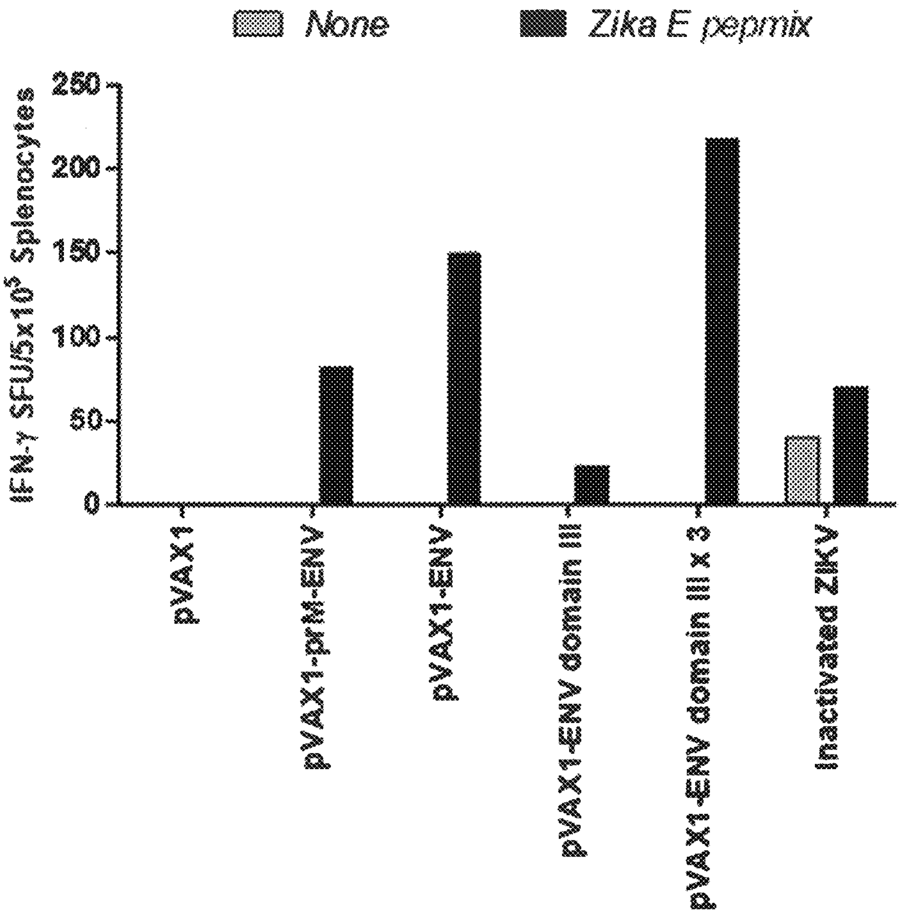
FIG. 6 shows the results of the analysis of a cellular immune response induced by a DNA vaccine candidate by measuring the degree of IFN-γ expression in splenocytes through ELISPOT.

The expression level of interferon-gamma (IFN-γ) in splenocytes was analyzed by ELISPOT, and the results are shown in FIG. 6. As shown in FIG. 6, the DNA vaccine candidates of the present invention showed a higher IFN-γ spot number than the pVAX1 control. In particular, Candidate 4 showed the highest expression level, which was significantly higher than Candidate 3 by five times or more.

Figure 7:
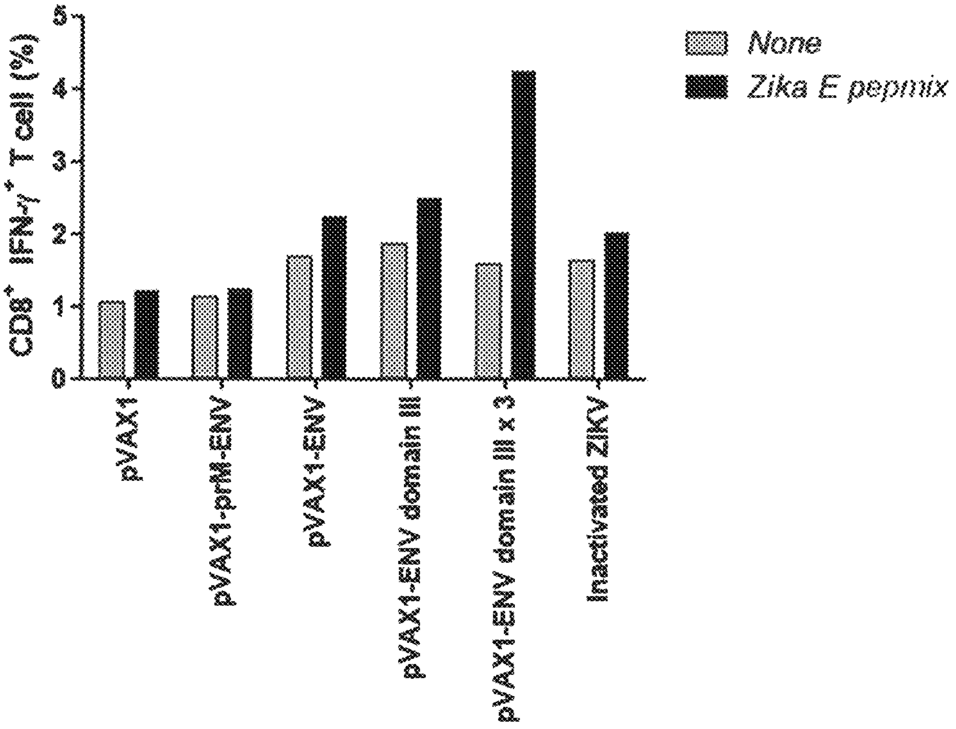
FIG. 7 shows the results of the analysis of a cellular immune response induced by a DNA vaccine candidate by measuring the degree of IFN-γ expression in T cells through FACS analysis.

In addition, the results of confirming IFN-γ expression in T cell through the flow cytometry (specifically, Fluorescence-Activated Cell Sorting (FACS)) analysis are shown in FIG. 7. As shown in FIG. 7, it can be seen that Candidate 4 shows the highest value.

Depositary authority name: Korea Research Institute of Bioscience and Biotechnology Accession number: KCTC13685BP Deposit date: Oct. 25, 2018

The invention claimed is:

1. A polynucleotide comprising SEQ ID NO: 1 encoding Zika virus E protein domain III repeatedly three times.

2. The polynucleotide according to claim 1, further comprising a polynucleotide of SEQ ID NO: 2 encoding an IgE signal peptide.

3. A recombinant expression vector comprising the polynucleotide according to claim 1.

4. A recombinant expression vector having a base sequence of SEQ ID NO: 3.

5. An isolated host cell comprising the recombinant expression vector according to claim 4.

6. The isolated host cell according to claim 5, characterized in that the host cell is *E. coli*-DH5α deposited as an accession number KCTC13685BP.

7. A composition that induces an immune response against Zika virus, comprising the polynucleotide according to claim 1.

8. The composition according to claim 7, characterized in that the polynucleotide further comprises a polynucleotide of SEQ ID NO: 2 encoding an IgE signal peptide.

9. The composition according to claim 7, further comprising an adjuvant.

10. The composition according to claim 7, characterized in that the composition induces a cellular or humoral immune response to Zika virus by expressing a Zika virus antigen protein.

11. The composition according to claim 7, characterized in that the composition induces a production of a neutralizing antibody against Zika virus by expressing a Zika virus antigen protein.

12. A composition that induces an immune response against Zika virus, comprising the recombinant expression vector according to claim 4.

13. The composition according to claim 12, further comprising an adjuvant.

14. The composition according to claim 12, characterized in that the composition induces a cellular or humoral immune response to Zika virus by expressing a Zika virus antigen protein.

15. The composition according to claim 12, characterized in that the composition induces a production of a neutralizing antibody against Zika virus by expressing a Zika virus antigen protein.

16. A method for preparing a neutralizing antibody against Zika virus, comprising (a) a step of administering the polynucleotide according to claim 1 to a mammalian excluding a human; and (b) a step of obtaining a neutralizing antibody that specifically binds to Zika virus from the mammalian.

17. The method for preparing a neutralizing antibody against Zika virus according to claim 16, further comprising (c) a step of humanizing the neutralizing antibody obtained in step (b).

* * * * *